(12) United States Patent
Tapocik

(10) Patent No.: US 10,441,057 B1
(45) Date of Patent: Oct. 15, 2019

(54) VIBRATING CAP REMOVABLY AFFIXED TO A CONTAINER RETAINING A VISCOUS SUBSTANCE

(71) Applicant: Bryan Tapocik, Highland, CA (US)

(72) Inventor: Bryan Tapocik, Highland, CA (US)

(73) Assignee: Innovative Product Brands, Inc., Highland, CA (US)

( * ) Notice: Subject to any disclaimer, the term of this patent is extended or adjusted under 35 U.S.C. 154(b) by 0 days.

(21) Appl. No.: 15/996,457

(22) Filed: Jun. 2, 2018

(51) Int. Cl.
*A45D 40/28* (2006.01)
*A61M 35/00* (2006.01)
*B65D 39/00* (2006.01)
*B65D 55/00* (2006.01)

(52) U.S. Cl.
CPC .......... *A45D 40/28* (2013.01); *A61M 35/003* (2013.01); *A45D 2200/20* (2013.01); *A45D 2200/207* (2013.01); *B65D 39/0052* (2013.01); *B65D 55/00* (2013.01)

(58) Field of Classification Search
CPC ............. A45D 40/265; A45D 40/28; A45D 2200/207; A45D 2200/20; A45D 34/045; A45D 34/06; A45D 2200/00; A45D 2200/10; A61M 35/003; A61M 35/00; B65D 39/0052; B65D 55/00
See application file for complete search history.

(56) References Cited

U.S. PATENT DOCUMENTS

| | | | | |
|---|---|---|---|---|
| 5,439,103 A | * | 8/1995 | Howes | B65D 5/4291 206/217 |
| 2006/0238338 A1 | * | 10/2006 | Nanda | B65D 41/34 340/540 |
| 2008/0203049 A1 | * | 8/2008 | Goldberg | A61J 9/00 215/11.1 |

* cited by examiner

*Primary Examiner* — David J Walczak
(74) *Attorney, Agent, or Firm* — Thomas I. Rozsa

(57) ABSTRACT

A vibrating cap that works in conjunction with a container that contains a viscous substance selected from the group consisting of pain relievers, muscle relaxants and medicine. A user can remove the upper vibrating cap from the lower body portion of the container, apply the contents of the container to a desired portion of the user's body, then place the cap onto the lower body portion of the container and turn the rotating cap portion on to vibrate. The user can then place the vibrating cap over the location where the viscous substance was applied for beneficial effects.

16 Claims, 5 Drawing Sheets

VIBRATING CAP REMOVABLY AFFIXED TO A CONTAINER RETAINING A VISCOUS SUBSTANCE

BACKGROUND OF THE INVENTION

1. Field of the Invention

The field of the invention relates to caps which are threaded onto or otherwise removably affixed to a container retaining a viscous substance such as pain relievers, muscle relaxants or medicine.

2. Description of the Prior Art

The inventor is unaware of any prior art that discloses the present invention.

SUMMARY OF THE INVENTION

The present invention is a vibrating cap that works in conjunction with a container that contains a viscous substance selected from the group consisting of pain relievers, muscle relaxants and medicine. A user can remove the upper vibrating cap from the lower body portion of the container, apply the contents of the container to a desired portion of the user's body, then place the cap onto the lower body portion of the container and turn the rotating cap portion on to vibrate. The user can then place the vibrating cap over the location where the viscous substance was applied for beneficial effects.

It is an object of the present invention to include a rotatable locking mechanism that allows the user to position the battery in the off position. During shipment, by positioning the battery in the off position, the vibrating cap will not accidentally be turned on and the battery will not be drained.

It is also an object of the present invention to provide a vibrating cap that is powered by a battery to cause an interior vibration member to transmit the vibration through the upper portion of the vibrating cap so that a user feels the vibration when the top of the cap is pressed against a user's body part.

It is an object of the present invention to include a rotatable locking mechanism that allows the user to position the battery in the off position. During shipment, by positioning the battery in the off position, the battery will not be accidentally turned on and the battery will not be drained.

A key feature of the present invention is the ability of a user to rotate the cap to the on position. When the cap is rotated to the on position, the vibrator will vibrate and transmit the vibration through the top when the top of the cap is pressed against a body part.

It is an additional object of the present invention to provide an activator arm that causes the vibration to occur when the activator is depressed and touches a battery.

It is a further object of the present invention to provide a two-piece upper vibrating cap that contains an upper vibrating portion and a lower housing portion.

It is still a further object of the present invention to provide a vibrating member that is strong enough to cause the vibration to be transmitted through the upper portion.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF EMBODIMENTS OF THE PRESENT INVENTION

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
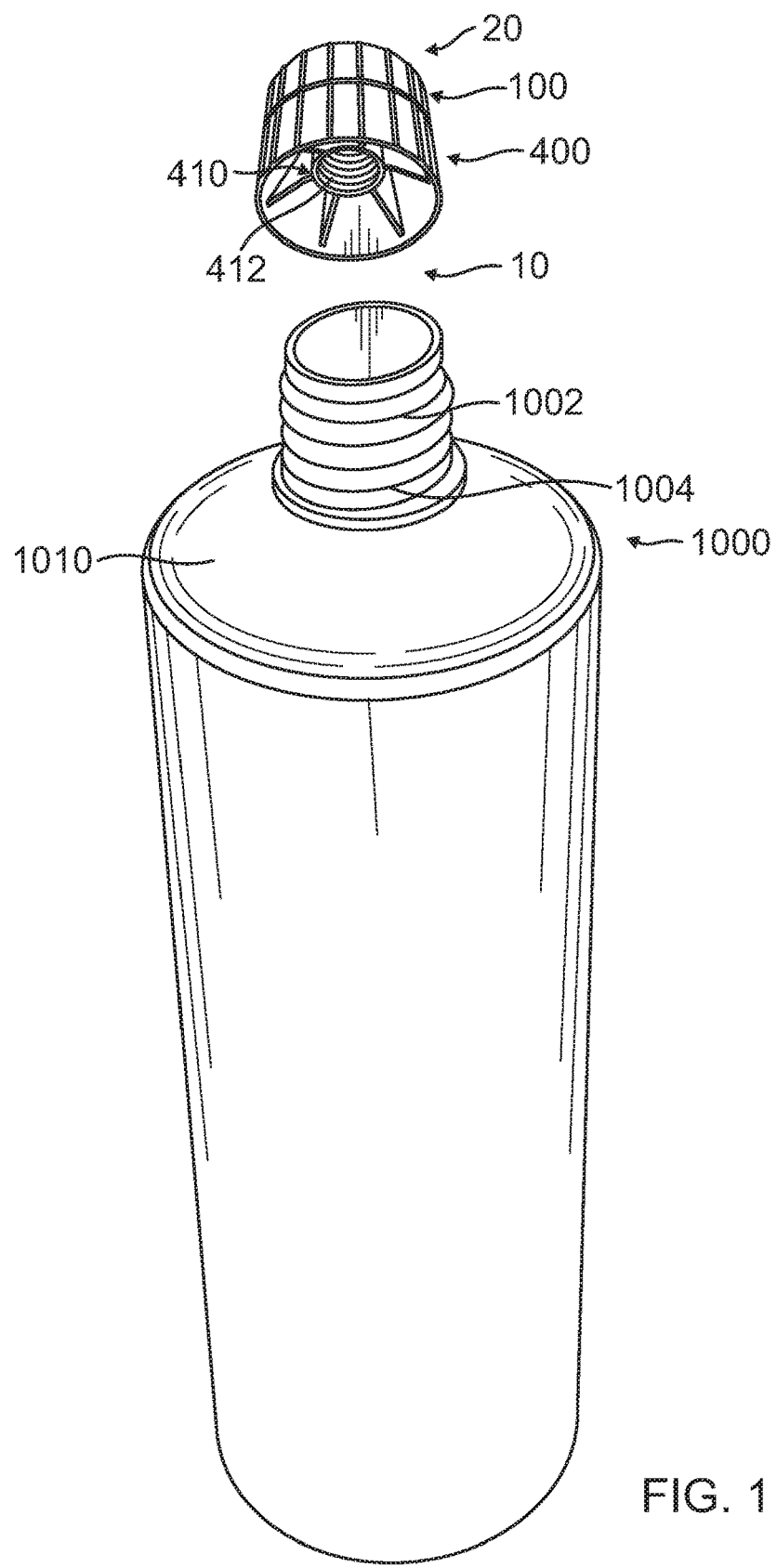
FIG. 1 is an exploded view of the present invention vibrating cap and container showing the two-piece cap being removed from the nozzle of the container.

Referring to FIG. 1, there is illustrated an exploded view of the present invention vibrating cap and container 10, having a two-piece cap 20 having an upper vibrating portion 100 and a lower housing portion 400. The present invention vibrating cap and container 10 also include a lower cylindrically shaped body portion 1000 having a nozzle 1002 with exterior threads 1004 located at a first end 1010 of the body portion 1000 with the nozzle 1002 sized to mate with a centrally located cylindrical opening 410 located in the lower housing portion 400. The cylindrical opening 410 includes mating threads 412 that engage and mate with threads 1004.

Figure 2A:
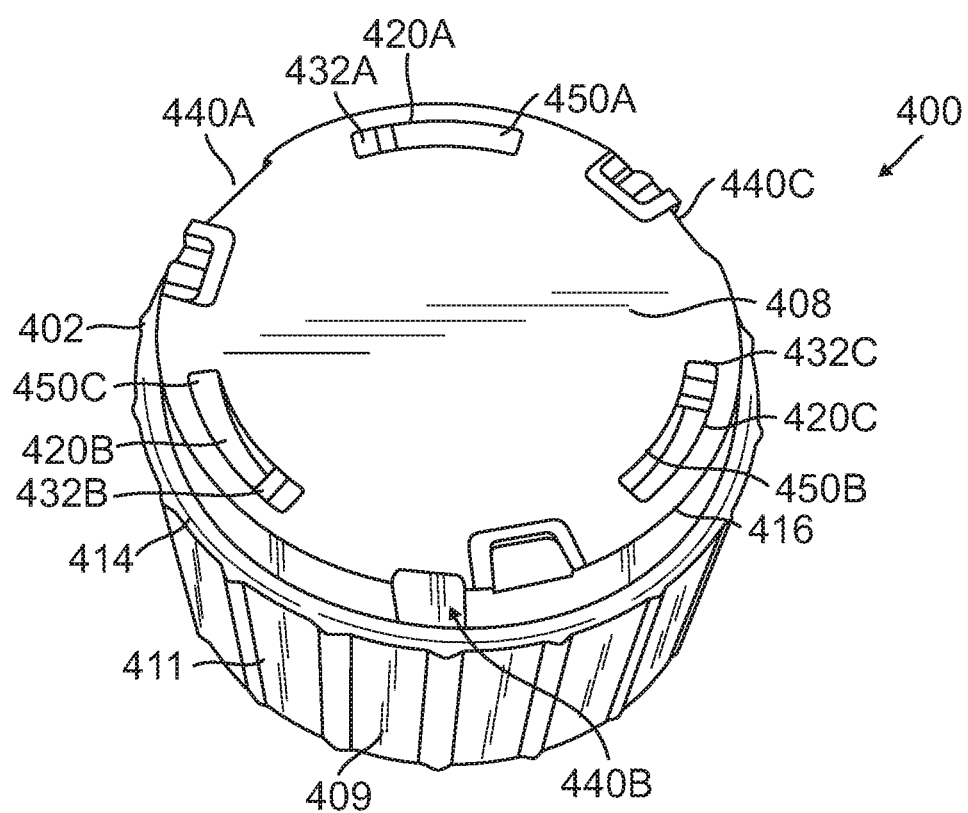
FIG. 2A is a top perspective view of the bottom portion of the vibrating cap.
Figure 2B:
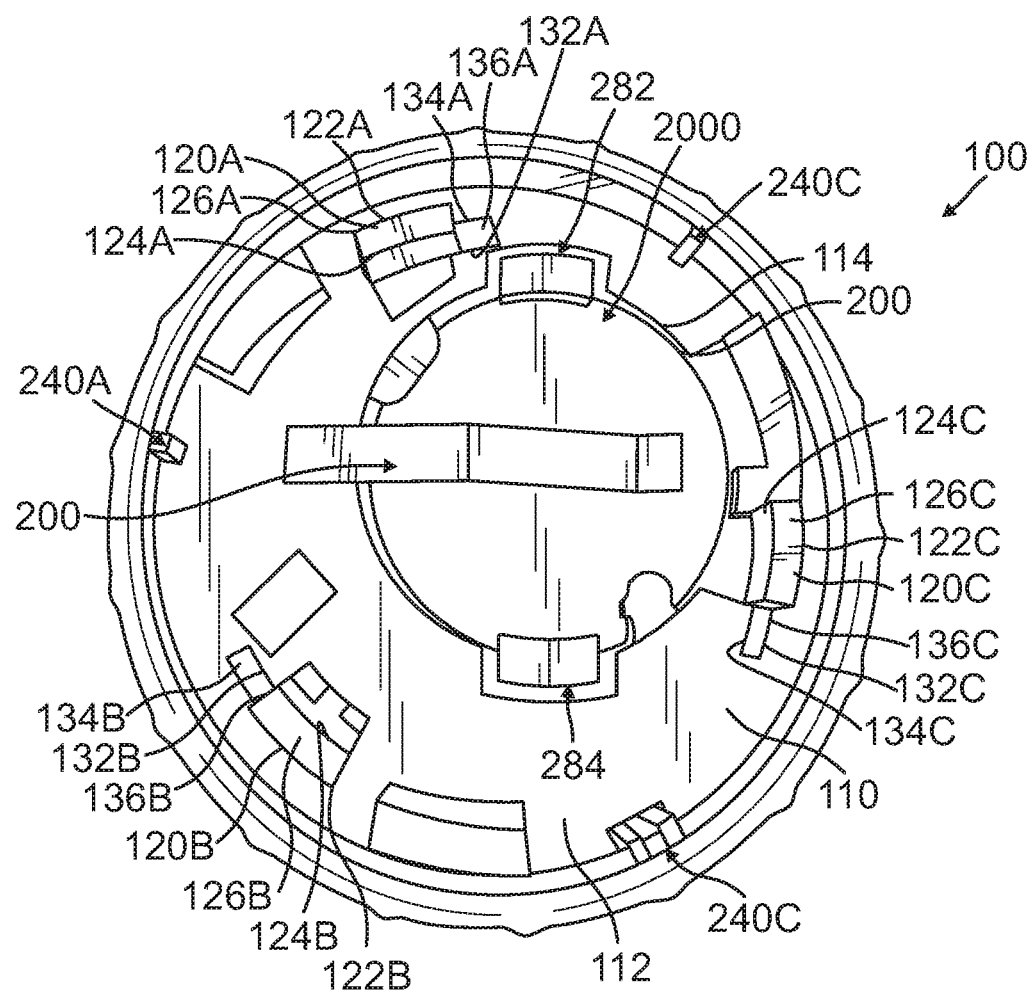
FIG. 2B is an interior perspective view of the top portion of the vibrating cap.
Figure 3:
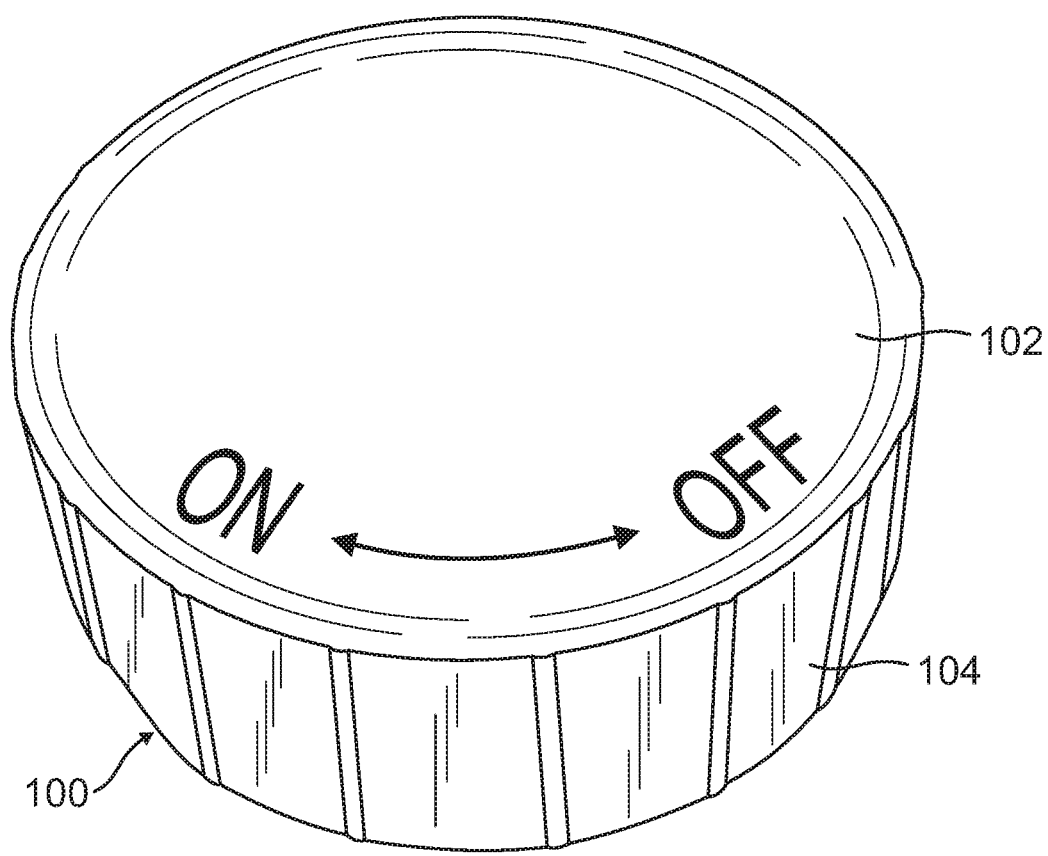
FIG. 3 is a top perspective view of the exterior top of the top portion of the vibrating cap.

Referring to FIG. 3, the upper vibrating portion 100 includes a top surface 102 that extends to a circumferential vertical sidewall 104 that surrounds an upper interior chamber 110 as illustrated in FIG. 2B. As also illustrated in FIG. 2B, the upper interior chamber 110 includes a generally horizontal surface 112 with a non-centrally located cutout 114 sized to receive a battery 2000, with said generally horizontal surface 112 having three equally spaced apart posts 120A, 120B, and 120C. Battery 2000 is removably retained within generally horizontal surface 112 by battery retaining members 282 and 284.

Rotation/Anti-Rotation

Figure 4:
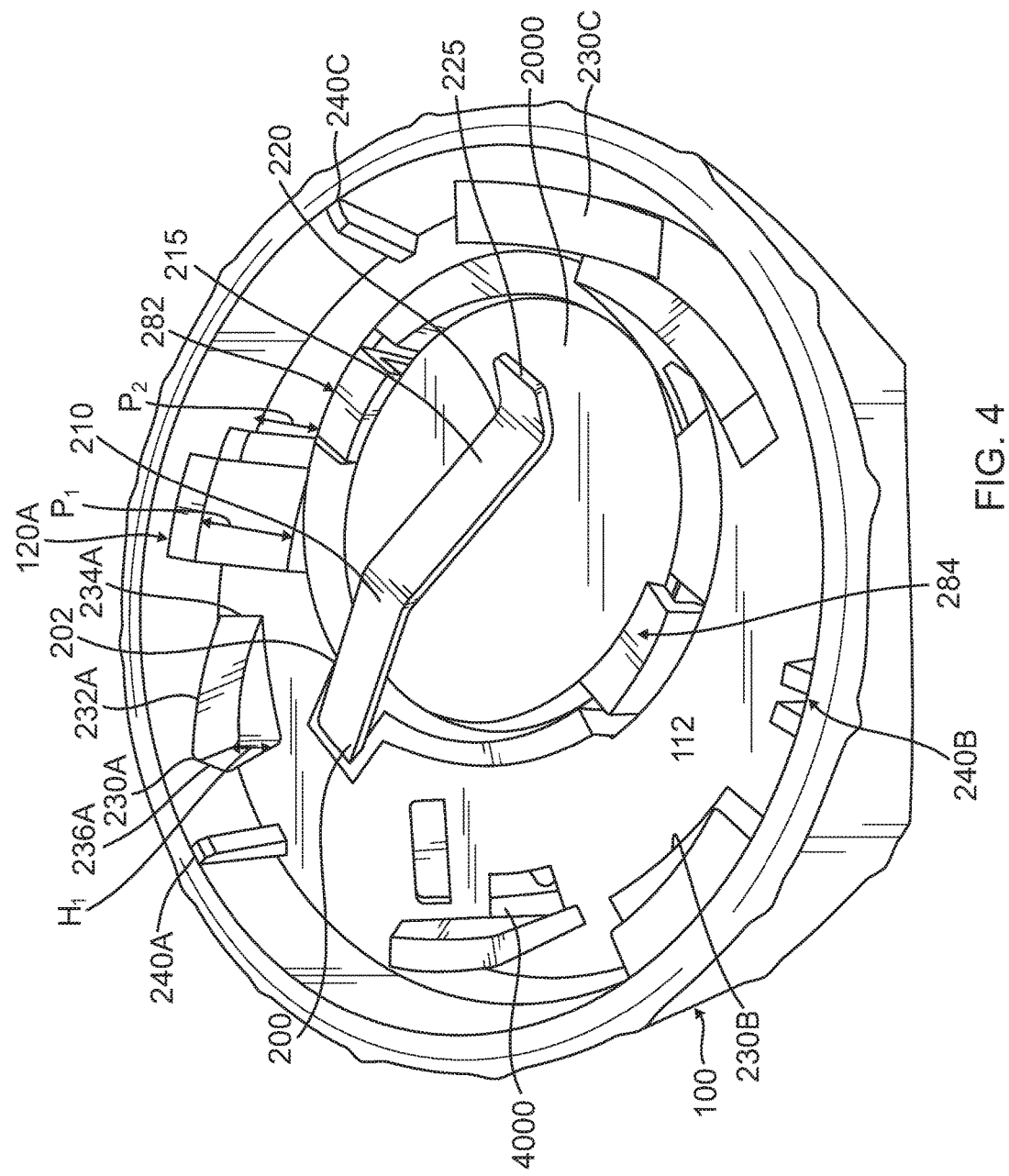
FIG. 4 is a closeup interior bottom perspective view of the top portion of the vibrating cap.

Referring to FIG. 2A, lower housing portion 400 has a circumferential vertical wall 411 that extends from a lower housing bottom section 409 to a housing horizontal shelf 414 and then upwardly to a second circumferential vertical wall 416. Positioned at approximate 120 degree interval spacing along second circumferential vertical wall 416 are three (3) channels 440A, 440B, and 440C. Channel 440A and channel 440C are equal in dimensions, however channel 440B is slightly larger to accommodate a double wall. Referring to FIGS. 3 and 4, upper vibrating portion or rotatable knob 100 has three (3) anti-rotational walls 240A, 240B, and 240C that fit within channels 440A, 440B, and 440C of lower housing portion 400 when the present invention vibrating cap and container 10 are in the closed condition. Anti-rotational walls 240A and 240C comprise a single wall; whereas, anti-rotational wall 240B comprises a double wall that will only fit within the larger channel 440B.

In the closed condition, upper vibrating portion or rotatable knob 100 can rotate clockwise from the off position approximately 1 degree to 5 degrees to the on position. This rotational distance is also equal to the distance between anti-rotational walls 240A, 240B, and 240C and the channel walls of channels 440A, 440B, and 440C.

Activation of the Vibrating Motor

Referring to FIGS. 2B and 4, post 120A has a first pair of vertical walls 122A and 124A that extend from horizontal surface 112 to a first horizontal wall 126A at a first post height P1. Post 120A has a second pair of vertical walls 132A and 134A that extend from horizontal surface 112 to a second horizontal wall 136A at a second post height P2. First horizontal wall 126A is higher than second horizontal wall 136A. Posts 120B and 120C are identical in shape and size but are positioned at a different location. Each post is positioned approximately 120 degrees apart from each other. For completeness, each post will be described in detail. Post 120B has a first pair of vertical walls 122B and 124B that extend from horizontal surface 112 to a first horizontal wall 126B at a first post height P1, Post 120B has a second pair of vertical walls 132B and 134B that extend from horizontal surface 112 to a second horizontal wall 136B at a second post height P2. First horizontal wall 126B is higher than second horizontal wall 136B. Lastly, Post 120C has a first pair of vertical walls 122C and 124C that extend from horizontal surface 112 to a first horizontal wall 126C at a first post height P1. Post 120C has a second pair of vertical walls 132C and 134C that extend from horizontal surface 112 to a second horizontal wall 136C at a second post height P2. First horizontal wall 126C is higher than second horizontal wall 136C.

Lower housing portion 400 has a lower housing top section 402 and a generally flat housing horizontal surface 408 containing three slots 420A, 420B, and 420C. Slots 420A, 420B, and 420C are positioned around housing horizontal surface 408 to correspond and receive posts 120A, 120B, and 120C. Slot 420A has a arcuate rectangular shape that extends downwardly to an interior chamber 450A on one end and extends to a horizontal ledge 432A on an opposite end. The length of horizontal ledge 432A is approximately equal to the length of second horizontal walls 136A. Similarly, slot 420B has an arced rectangular shape that extends downwardly to an interior chamber 450B on one end and extends to a horizontal ledge 432B on an opposite end. The length of horizontal ledge 432B is approximately equal to the length of second horizontal wall 136B. Lastly, slot 420C has a arced rectangular shape that extends downwardly to an interior chamber 450C on one end and extends to a horizontal ledge 432C on an opposite end. The length of horizontal ledge 432C is approximately equal to the length of second horizontal wall 136C.

Upper vibrating portion or rotatable knob 100 rotates between 1 degree and 5 degrees to turn the present invention vibrating cap and container 10 from the off position to the on position. In the off position, first horizontal walls 126A, 126B, and 126C of posts 120A, 120B, and 120C are positioned directly over horizontal ledges 432A, 432B, and 432C. In the off position upper vibrating portion or rotatable knob 100 cannot be pressed downward to cause the activator bar 200 to press down on the battery 2000 because first horizontal walls 126A, 126B, and 126C abut directly against horizontal ledges 432A, 432B, and 432C. In the on position, however, second horizontal walls 136A, 136B, and 136C, which have shorter connecting vertical walls 132A, 134A, 132B, 134B, 132C, and 134C, which do not directly abut against horizontal ledges 432A, 432B, and 432C because of the vertical gap between horizontal ledges 432A, 432B, and 432C and second horizontal walls 136A, 136B, and 136C when the present invention vibrating cap and container 10 is in the on position.

Referring to FIG. 4, there is illustrated an interior perspective closeup view of the upper vibrating portion or rotatable knob 100. When in the on position and a user presses downward on the present invention vibrating cap and container 10, the vertical gap that is between horizontal ledges 432A, 432B, and 432C and second horizontal walls 136A, 136B, and 136C is reduced causing bar upper ridge 210 of activator bar 200 to move upwardly when contacted by housing horizontal surface 408. Activator bar 200 has a downwardly sloped rectangular section 202 that extends from horizontal surface 112 to a bar upper ridge 210 and then has an upwardly sloped section 215 that extends upwardly to angled contact point 220. Activator bar 200 ends in a downwardly sloped end section 225, When contact point 220 touches battery 2000 the circuit is completed and vibrating motor 4000 causes the top surface 102 to vibrate as the vibration is transmitted through the top surface 102.

Also occurring during the depressing of upper vibrating portion or rotatable knob 100, is the compression of leaf springs 230A, 230B, and 230C. All of the leaf springs function identically; therefore only leaf spring 230A will be explained in detail. Leaf springs 230B and 230C function the same way. Referring to FIG. 4, leaf spring 230A is shown in the initial or resting position having a rectangular spring arm 232A having a pivot connection 234A that connects rectangular spring arm 232A to horizontal surface 112 at a first end. Rectangular spring arm 232A has a leaf spring opposite or second end 236A that extends downward to a height H1. When upper vibrating portion or rotatable knob 100 is in the on position and pushed downward, leaf spring second end 236A is compressed to reduce the height of H1 and allow second end 236A to be flush or nearly flush with horizontal surface 112. Leaf Springs 230B and 230C function identically to leaf spring 230A. When a user releases the downward force on upper vibrating portion or rotatable knob 100, the force of the leaf springs, 230A, 230B, and 230C, return upper vibrating portion or rotatable knob 100 to its initial resting position elevated above lower housing portion 400. The approximate distance of travel after the user releases the downward force placed on upper vibrating portion or rotatable knob 100 is between one (1) millimeter and three (3) millimeters.

In operation a user can open the present invention vibrating cap and container 10 by unscrewing the two-piece cap 20 and squeezing a desired amount of medicated liquid or medicated gel from the lower body portion 1000 through nozzle 1002 and onto the user's skin. The user can then screw the two-piece cap 20 back onto the nozzle 1002 of lower body portion 1000. While the body portion 1000 is illustrated as cylindrical, it will be appreciated that other shapes such as elliptical and oval are within the spirit and scope of the present invention. Lastly, the user can rotate the upper vibrating portion or rotatable knob 100 to the on position to enact the vibrating motor. Then, the user can apply and receive the benefits of the medicated cream being applied with a vibrating applicator.

It is also within the spirit and scope of this invention for the number of posts, number of channels, number of anti-rotational walls, number of leaf springs, and number of slots to be a number not equal to three (3) as disclosed in detail above. Therefore, it is within the spirit and scope of this invention for the number of the elements stated in this paragraph to be equal to two (2) or four (4).

In one preferred embodiment, the lower cylindrically shaped body portion 1000 is made of material selected from the group consisting of rolled laminated plastic and rolled laminated aluminum each having from one (1) to eight (8) layers of rolled laminated plastic or aluminum. The plastic is selected from the group consisting of polypropylene, polyethylene, polyvinyl or combinations including one or more of these plastics. It is also within the spirit and scope of the present invention for the lower cylindrically shaped body portion 1000 to be made of other metal materials.

Of course the present invention is not intended to be restricted to any particular form or arrangement, or any specific embodiment, or any specific use, disclosed herein, since the same may be modified in various particulars or relations without departing from the spirit or scope of the claimed invention herein above hereinabove shown and described of which the apparatus or method shown is intended only for illustration and disclosure of an operative embodiment and not to show all of the various forms or modifications in which this invention might be embodied or operated.

What is claimed is:

1. A container comprising:
   a. a two-piece cap having an upper vibrating portion and a lower housing portion;
   b. a lower cylindrically shaped body portion having a nozzle with exterior threads located at a first end with said nozzle sized to mate with mating threads in a centrally located cylindrical opening located in said lower housing portion;
   c. said upper vibrating portion having a top surface that extends to a vertical sidewall that surrounds an upper interior chamber;
   d. said upper interior chamber containing a generally flat surface with a non centrally located cutout sized to receive a battery, with said generally flat surface having three equally spaced apart posts;
   e. each said spaced apart post having a first pair of vertical walls that extend from a horizontal surface to a first horizontal wall having a first height and a second pair of vertical walls that extend from said horizontal surface to a second horizontal wall having a second height;
   f. first horizontal wall is higher than second horizontal wall;
   g. each post is positioned approximately 120 degrees apart;
   h. said lower housing portion has a lower housing top section and a housing horizontal surface including three slots positioned around said housing horizontal surface to correspond and receive each said spaced apart post;
   i. each slot having an arced rectangular shape that extends downwardly to an interior chamber on one end and extends to a corresponding horizontal ledge on an opposite end;
   j. said lower housing portion has a circumferential vertical wall that extends from a lower housing bottom section to a housing horizontal shelf and then upwardly to a second circumferential vertical wall;
   k. said second circumferential vertical wall having three channels positioned at approximate 120 degree interval spacing along said second circumferential vertical wall;
   l. said upper vibrating portion has three anti-rotational walls that fit within said three channels with one of the rotational walls being a double wall;
   m. said upper vibrating portion including a battery, an activator bar and a vibrating motor;
   n. in an off position, the first horizontal walls of said posts are positioned directly over each horizontal ledge and abut directly against each horizontal ledge; and
   o. in an on position, said first horizontal walls of each of said spaced apart posts are positioned directly over a respective interior chamber facilitating said activator bar to press down on the battery and complete a circuit to activate said vibrating motor.

2. The container in accordance with claim 1, further comprising: a gap between each second horizontal wall and each horizontal ledge when said upper vibrating portion is in the on position.

3. The container in accordance with claim 1, further comprising: said upper vibrating portion rotates between 1 degree and 5 degrees.

4. The container in accordance with claim 1, further comprising: said upper vibrating portion rotates clockwise from the off position to the on position.

5. The container in accordance with claim 1, further comprising: said lower cylindrically shaped body portion is made of material selected from the group consisting of rolled laminated plastic and rolled laminated aluminum.

6. A container comprising:
   a. a two-piece cap having an upper vibrating portion and a lower housing portion;
   b. a lower body portion having a nozzle with exterior mating members located at a first end with said nozzle sized to mate with corresponding mating members centrally located in a cylindrical opening located in said lower housing portion;
   c. said upper vibrating portion having a top surface that extends to a vertical sidewall that surrounds an upper interior chamber;
   d. said upper interior chamber including a generally flat surface with a non-centrally located cutout sized to receive a battery, with said generally flat surface having a multiplicity of spaced apart posts;
   e. each said multiplicity of spaced apart posts having a first pair of vertical walls that extend from a horizontal surface to a first horizontal wall having a first height and a second pair of vertical walls that extend from said horizontal surface to a second horizontal wall having a second height;
   f. first horizontal wall is higher than second horizontal wall;
   g. said lower housing portion including a lower housing top section and a housing horizontal surface containing a multiplicity of slots positioned around said housing horizontal surface to correspond and receive a respective one of each said multiplicity of spaced apart posts;
   h. each of said multiplicity of slots extending downwardly to an interior chamber on one end and extends to a corresponding horizontal ledge on an opposite end;
   i. said lower housing portion having a circumferential vertical wall that extends from a lower housing bottom section to a housing horizontal shelf and then upwardly to a second circumferential vertical wall;
   j. said second circumferential vertical wall having a multiplicity of spaced apart channels positioned along said second circumferential vertical wall;
   k. said upper vibrating portion having a multiplicity of anti-rotational walls with a respective anti-rotation wall fitting within a respective channels;
   l. said upper vibrating portion including a battery, an activator bar and a vibrating motor;

m. in an off position, the first horizontal walls of each of said multiplicity of posts are positioned directly over each horizontal ledge and abut directly against each horizontal ledge; and n. in an on position, said first horizontal walls of each of said spaced apart multiplicity of posts are positioned directly over a respective interior chamber facilitating said activator bar to press down on the battery and complete a circuit to activate said vibrating motor.

7. The container in accordance with claim 6, further comprising: a gap between each second horizontal wall and each horizontal ledge when said upper vibrating portion is in the on position.

8. The container in accordance with claim 5, further comprising: said upper vibrating portion rotates between 1 degree and 6 degrees.

9. The container in accordance with claim 6, further comprising: said upper vibrating portion rotates clockwise from the off position to the on position.

10. The container in accordance with claim 6, further comprising: at least one of the multiplicity of anti-rotational walls is a double wall.

11. The container in accordance with claim 6, further comprising: said lower body portion is made of material selected from the group consisting of rolled laminated plastic and rolled laminated aluminum.

12. A container comprising:
   a. a two-piece cap having an upper vibrating portion and a lower housing portion;
   b. a lower body portion having a nozzle with exterior threads located at a first end with said nozzle sized to mate with a centrally located cylindrical opening located in said lower housing portion;
   c. said upper vibrating portion having a top surface that extends to a vertical sidewall that surrounds an upper interior chamber;
   d. said upper interior chamber containing a generally flat surface with a non-centrally located opening to receive a battery, with said generally flat surface having at least two spaced apart posts;
   e. each said spaced apart post having a first pair of vertical walls that extend from a horizontal surface to a first horizontal wall having a given height and a second pair of vertical walls that extend from said horizontal surface to a second horizontal wall having another height;
   f. first horizontal wall is higher than second horizontal wall;
   g. said lower housing portion has a lower housing top section and a housing horizontal surface containing at least two slots positioned around said housing horizontal surface to correspond and receive each said spaced apart post;
   h. each slot extends downwardly to an interior chamber on one end and extends to a corresponding horizontal ledge on an opposite end;
   i. said lower housing portion has a circumferential vertical wall having at least two channels positioned along said vertical wall;
   j. said upper vibrating portion has at least two anti-rotational walls that fit within said at least two channels;
   k. said upper vibrating portion including a battery, an activator bar and a vibrating motor;
   l. in an off position, the first horizontal walls of said posts are positioned directly over each horizontal ledge and abut directly against each horizontal ledge; and
   m. in an on position, said first horizontal walls of each of said spaced apart posts are positioned directly over a respective interior chamber facilitating said activator bar to press down on the battery and complete a circuit to activate said vibrating motor.

13. The container in accordance with claim 12, further comprising: a gap between each second horizontal wall and each horizontal ledge when said upper vibrating portion is in the on position.

14. The container in accordance with claim 12, further comprising: said upper vibrating portion rotates between 1 degree and 5 degrees.

15. The container in accordance with claim 12, further comprising: said upper vibrating portion rotates clockwise from the off position to the on position.

16. The container in accordance with claim 12, further comprising: said lower body portion is made of material selected from the group consisting of rolled laminated plastic and rolled laminated aluminum.

\* \* \* \* \*